United States Patent
Chen

(10) Patent No.: US 8,329,963 B2
(45) Date of Patent: Dec. 11, 2012

(54) REMOVING SOLIDS IN MONOETHYLENE GLYCOL RECLAMATION

(75) Inventor: James C. T. Chen, Houston, TX (US)

(73) Assignee: Cameron International Corporation, Houston, TX (US)

( * ) Notice: Subject to any disclaimer, the term of this patent is extended or adjusted under 35 U.S.C. 154(b) by 322 days.

(21) Appl. No.: 12/671,263

(22) PCT Filed: Jul. 17, 2008

(86) PCT No.: PCT/US2008/070268
§ 371 (c)(1),
(2), (4) Date: Jan. 29, 2010

(87) PCT Pub. No.: WO2009/017971
PCT Pub. Date: Feb. 5, 2009

(65) Prior Publication Data
US 2010/0191023 A1 Jul. 29, 2010

Related U.S. Application Data

(60) Provisional application No. 60/952,716, filed on Jul. 30, 2007.

(51) Int. Cl.
*C07C 29/74* (2006.01)
*B01J 8/00* (2006.01)
(52) U.S. Cl. ........................................ 568/920; 422/187
(58) Field of Classification Search .................. 568/920; 422/187
See application file for complete search history.

(56) References Cited

U.S. PATENT DOCUMENTS 4,822,926 A * 4/1989 Dye ............................. 568/867
7,232,505 B2 * 6/2007 Laborie et al. .................. 203/18

OTHER PUBLICATIONS

C. A. Nazzer, et al., "Advances in Glycol Reclamation Technology," OTC 18010, 2006 Offshore Technology Conference, Houston, Texas, May 1-4, 2006., p. 1.
COMART, "MEG Regeneration" Technical Bulletin, 2007, available from: www.comart.biz/work0/pb/pb-42-file-meg_regeneration.pdf.
K. Van Son, et al., "Reclamation/Regeneration of Glycols Used for Hydrate Inhibition," Deep Offshore Technology 2000.

* cited by examiner

*Primary Examiner* — Sikarl Witherspoon
(74) *Attorney, Agent, or Firm* — Mossman Kumar & Tyler PC

(57) ABSTRACT

The seeding of calcium carbonate into a calcium chloride-contaminated monoethylene glycol (MEG) stream accelerates the growth of calcium carbonate particles to a size that enhances their removal from the stream by filtration. A seeding vessel allows the calcium carbonate particles a time period to grow. Sodium carbonate may be added to the contaminated stream to facilitate calcium carbonate particle growth. A recycle seeding conduit may recycle seeds from a filtration unit to the seeding vessel. A base such as sodium hydroxide may be added to accelerate the precipitation process.

16 Claims, 1 Drawing Sheet

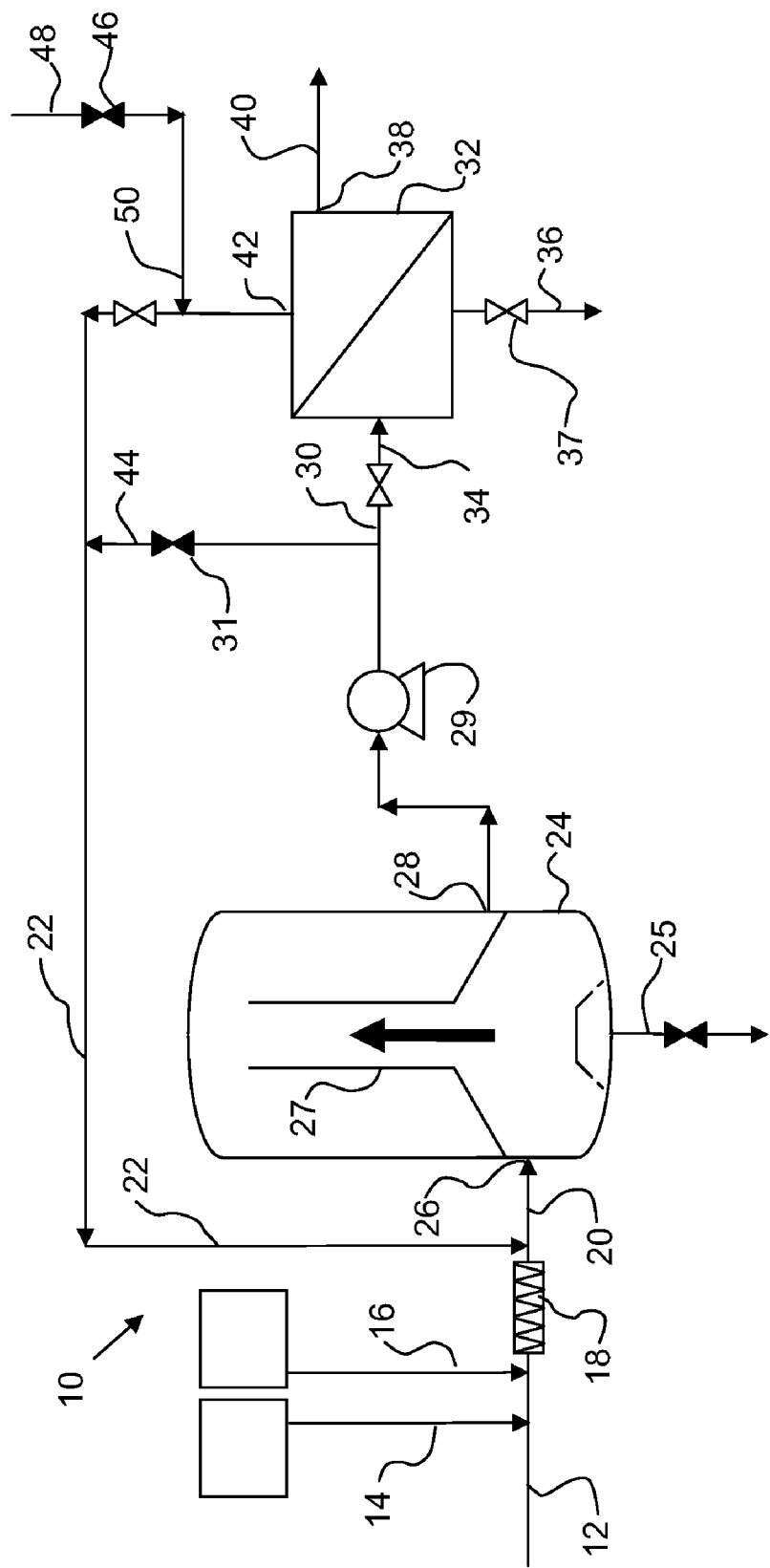

REMOVING SOLIDS IN MONOETHYLENE GLYCOL RECLAMATION

CROSS REFERENCE TO RELATED APPLICATIONS

This application claims priority from PCT/US2008/070268, filed Jul. 17, 2008, and from U.S. Provisional Application Ser. No. 60/952,716, filed Jul. 30, 2007 each of which are incorporated herein by reference.

BACKGROUND OF THE INVENTION

The present invention relates to methods and apparatus for reclaiming or recovering glycols, and more particularly relates, in one non-limiting embodiment, to methods and apparatus for reclaiming or recovering monoethylene glycol by removing salts therefrom.

For several decades monoethylene glycol (MEG) and methanol have been the primary chemicals injected offshore to inhibit the formation of hydrates in oil and gas production pipelines and related facilities. At fields that require persistent inhibition, the cost of replacing hydrate inhibitor chemical that is lost to the gas and hydrocarbon liquid product streams is a determining factor in selecting the inhibitor. Methanol solubility in gas and liquid hydrocarbon product streams may be two or more orders of magnitude higher than MEG solubility. This creates a strong economic incentive to use MEG despite the greater quantity of MEG needed per degree of hydrate temperature suppression. Further, methanol is an unwanted contaminant in hydrocarbon sales products.

Nevertheless, the adoption of MEG over methanol has taken some time to occur, due in part to familiarity with methanol and perceptions in operating difficulties in recovering and recycling MEG. There have been concerns about detrimental effects that saline formation water had on conventional MEG reconcentrator units. Salts are non-volatile, and they will remain in the lean MEG during regeneration as the water is boiled off. If salt enters the MEG system with production fluids, either continuously or in periodic slugs, its concentration in the system will increase during each regeneration cycle until the solubility limit is finally reached and precipitation occurs. Unless MEG is reclaimed by removing the salt, serious fouling and plugging of equipment and flowlines may result. Depending on the magnitude of the contamination problem, MEG reclamation may be accomplished by either continuous or intermittent (i.e. batch) removal from either the total circulation stream or else a partial stream.

Many MEG reclamation projects involve the removal or reduction of alkaline earth metal salts such as calcium chloride ($CaCl_2$) from the contaminated MEG stream. In some reclamation efforts, the salts are converted to carbonates which may be removed as precipitated particulates. Current or conventional removal methods used include centrifuges, diatomaceous earth (DE) filtration and separation tanks with relatively long retention times (e.g. on the order of 10 hours).

It would be desirable if methods and apparatus were devised that could easily remove salts and/or carbonates from MEG streams with greater efficiency than at present.

BRIEF SUMMARY OF THE INVENTION

There is provided, in one non-restrictive form, an exemplary MEG reclamation apparatus that includes a seeding vessel with a vessel inlet and a vessel outlet, where the vessel inlet is adapted to receive a mixture from a mixture conduit. The apparatus further includes a filtration unit having a feed inlet, a solids outlet, a recycle outlet and a permeate outlet. Also included in the apparatus is a seeded effluent conduit from the vessel outlet to the feed inlet on the filtration unit, as well as a recycle conduit from the recycle outlet of the filtration unit to the mixture conduit.

In another non-restrictive example, there is provided a method for reclaiming MEG that includes contacting an alkaline earth metal salt-contaminated MEG stream with an alkali metal carbonate and a base (accelerator) to form a mixture. The mixture may be contacted with recycled alkaline earth metal carbonate seeds to form a feed. The feed is routed to a seeding vessel for growing alkaline earth metal carbonate particles. A seeded effluent of relatively large particles is transmitted from the seeding vessel to a filtration unit. Alkaline earth metal carbonate solids are discharged from the filtration unit. A relatively reclaimed MEG stream is produced from the filtration unit. Alkaline earth metal carbonate seeds are recycled from the filtration unit to the feed.

BRIEF DESCRIPTION OF THE DRAWING

FIG. 1 is a schematic illustration of a MEG reclamation system showing one non-limiting embodiment of the recycle seeding apparatus herein.

It will be appreciated that the FIGURE is a schematic illustration that is not to scale or proportion, and, as such, some of the important parts of the invention may be exaggerated for illustration.

DETAILED DESCRIPTION OF THE INVENTION

In a MEG reclamation system, sodium carbonate ($Na_2CO_3$) is injected into a MEG stream containing an alkali metal salt such as calcium chloride ($CaCl_2$) to precipitate calcium carbonate ($CaCO_3$) from the MEG solution to reduce or eliminate $CaCO_3$ deposition on the heating element of a downstream MEG feed preheater prior to the MEG flash separator of a typical MEG reclamation system. However, the $CaCO_3$ particles formed are very small in size, on the order of 2-5 microns in average particle size and thus they are difficult to filter out. It has been discovered that by seeding the $CaCO_3$ in a MEG solution, the $CaCO_3$ will form crystals or larger particles which are easier to separate and filter out.

Non-limiting exemplary methods and apparatus described herein enhance the removal of a salt from a MEG stream intermixed therewith by means of salting the contaminated stream with carbonate seeds, and then letting the carbonate particles grow in size in a seeding vessel. The relatively larger size of the carbonate particles makes it easier to subsequently separate them from the MEG stream to reclaim and recover a relatively purified, reclaimed MEG stream.

The method and apparatus herein are expected to be useful in reclaiming any MEG stream contaminated with a salt, although the chemistry of creating the particles may be different depending on the salts involved.

The MEG reclamation apparatus described herein may be part of a larger MEG reclamation system that may be used to recondition, reclaim or recover a relatively pure MEG stream. Such MEG reclamation systems may typically include a wet MEG surge drum, one or more wet MEG coalescing filters, a MEG feed preheater, a MEG flash separator, a salt handling system and at least one MEG distillation column, serially connected by lines or conduits transmitting a MEG stream in various stages of recovery. The MEG reclamation apparatus herein would replace the wet MEG coalescing filter(s). The stream egressing from the wet MEG surge drum would feed into the MEG reclamation apparatus as contaminated glycol stream 12 described herein, which in turn would feed the relatively pure MEG stream 40 (permeate) into the MEG preheater, where the heated stream would be fed to the MEG flash separator, where the flashed light components would go to the MEG distillation column. It should also be appreciated that it is not necessary for all of the contaminating salt(s) to be removed from the MEG stream for the apparatus and method described herein to be considered a success, although complete removal would certainly be a worthwhile goal. In one non-limiting embodiment, an objective herein is to remove $CaCO_3$ particles from the MEG stream to a concentration of 10 ppm or less.

The overall MEG reclamation apparatus herein is generally referred to in FIG. 1 as 10. Contaminated MEG stream enters via line 12, which in one non-limiting embodiment herein is MEG containing an undesirable level of calcium chloride ($CaCl_2$). To contaminated MEG stream 12 may be added sodium carbonate ($Na_2CO_3$) via line 14 and a base, in one non-restrictive version an alkali metal hydroxide such as sodium hydroxide (NaOH) via line 16. The base acts as an accelerator to enhance the precipitation process. These components may be optionally mixed in mixer 18 egressing to mixture conduit 20.

To mixture stream 20 is added recycle seeding stream from conduit 22, which as will be explained is an effluent from the seeding vessel 24 or a seeded effluent of $CaCO_3$ particles to provide seeds for building relatively larger particles or crystals in seeding vessel 24. Seeding vessel 24 has vessel inlet 26 and vessel outlet 28, where the inlet 26 receives the mixture from mixture conduit 20. Seeding vessel 24 may be preloaded with MEG containing formed $CaCO_3$ crystals. This preloading may occur before the start-up of system operations. The mixture remains in seeding vessel 24 to grow $CaCO_3$ particles to a relatively larger size. Conventionally, $CaCO_3$ particles are in the range of 2-5 microns in average particle size, whereas in the apparatus and method herein, the particles or crystals may grow to at least about 10 microns or larger, and in an alternate non-limiting embodiment may grow to at least about 15 microns, in another non-restrictive version to at least about 20 microns or larger, possibly 30 microns or larger, or even about 40 microns or larger. A typical flow rate through the seeding vessel 24 ranges from about 40 gallons per minute (gpm) to about 120 gpm (about 150 to about 455 liters per minute). In another non-restrictive version the residence time in seeding vessel 24 may range from about 5 to about 10 minutes, alternatively from about 20 independently to about 30 minutes. Seeding vessel 24 may be provided with solids drain line 25.

Seeded effluent conduit 30 containing effluent from seeding vessel 24 which effluent contains relatively larger particles, extends from vessel outlet 28 to filtration or separation unit 32 at feed inlet 34 via pump 29. Solids ($CaCO_3$) are rejected at solids outlet 36, such as during a flushing or cleaning operation described below, permeate outlet 38 egresses relatively pure MEG (permeate) stream 40, where recycle seeding conduit 22 exits recycle outlet 42 provides a recycled seeded effluent of $CaCO_3$ seeds back to mixture in conduit 20 as previously described. In one non-restrictive embodiment, the size of the particles in the seeded effluent exiting outlet 42 is about 20 microns or higher. Solids outlet line 36 may also be used to back flush the filtration unit 32 when high delta pressure in the filtration unit 32 reaches 15 psig (103 kPa) or higher, in one non-limiting embodiment. The seeds or particles in this stream may also be about 20 microns or higher in average particle size. Filtration unit 32 may be a microfiltration unit or any other suitable filtration or separation unit including, but not necessarily limited to, any kind of cross-flow filter and the like. The filter elements for filtration unit 32 may be rated from about 5 to about 10 microns, in one non-limiting embodiment, alternatively from about 10 independently to about 15 in another non-restrictive version.

There is optionally provided a large particle-containing seeded effluent recycle line 44 from the large particle-containing seeded effluent conduit 30 to the recycle seeding conduit 22. Particle seeded effluent recycle line 44 is generally used only during preloading of the $CaCO_3$ particles into seeding vessel 24 when recirculation may be required.

In the particular embodiment illustrated, the reaction may be schematically outlined as:

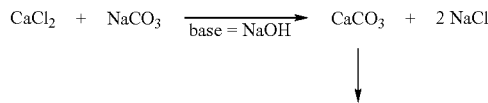

One non-limiting embodiment of the process for reclaiming MEG involves the following operations.

$CaCO_3$ Crystal Preparation Before Start Up

The seeding vessel 24 will be loaded with predetermined concentration of MEG and $CaCO_3$ crystal. This mixture will be pumped through line 28, pump 29, valve 31 (which is normally closed during regular or normal operation) line 44, 20 and vessel inlet 26 into the seeding vessel 24. The pumping will last approximately 10 to 20 minutes, in one non-limiting version. It should be noted that seeding vessel 24 may be sized for approximately 5 to 10 minutes retention time, in one non-limiting embodiment.

Normal Operation

The MEG and $CaCl_2$ mixture will flow in line 12. $Na_2CO_3$ will be added through line 14. NaOH (or other base) may be added in line 16 to accelerate the precipitation of $CaCO_3$, if required. The mixture will be mixed by mixer 18 and flow through line 20 and vessel inlet 26.

The mixture of MEG and freshly precipitated particles (approximately 2-5 micron size) will flow into the seeding vessel 24. The mixture flow will flow in the direction of the large arrow over the baffle 27 (more than one baffle may be present), the flow containing mainly MEG and some larger particles due to the seeding effect of the crystals. This MEG and the larger particles will be pumped by pump 29 through lines 30 and 34 to the filtration unit 32 (e.g. a cross-flow filter). In one non-limiting embodiment, the vessel will contain many filter elements. The mixture will flow inside the element(s) and the permeate (clean MEG) will flow through the wall(s) of the element(s). The more concentrated particles will be recycled back to the seeding vessel 24.

The permeate (MEG free from particles) will flow out line 40. A portion of the mixture will be recycled and flow through lines 42, 22 and vessel inlet 26. It should be noted that the recycled flow will contain more concentrated particles. When the pressure difference of the filtration unit 32 exceeds a predetermined pressure, in one non-restrictive embodiment about 15 psig (103 kPa) due to some of the solids adhering the filter elements, a purging or cleaning operation may be performed.

Purging Operation

When pressure difference exceeded about 15 psig (103 kPa) e.g., pump 29 will stop. The filtration unit 32 will be drained through line 36 and open (normally closed) filtration unit drain valve 37. During draining, all lines will be closed with the exception of line 36 and brine feed purge lines 48 and 50 and purge will be open via normally-closed valve 46 and normally closed drain valve 37. A clean brine under pressure will flow through purge lines 48, 50 and inside the filter element(s) scrubbing the solids from the wall(s) of the filter element(s). The mixture of solids and brine will be directed to drain 36.

In the foregoing specification, the invention has been described with reference to specific embodiments thereof, and is expected to be effective in providing methods and apparatus for reclaiming MEG streams more efficiently. However, it will be evident that various modifications and changes can be made thereto without departing from the broader scope of the invention as set forth in the appended claims. Accordingly, the specification is to be regarded in an illustrative rather than a restrictive sense. For example, the seeding vessel may be changed or optimized from that illustrated and described, and even though they were not specifically identified or tried in a particular system, would be anticipated to be within the scope of this invention. For instance, the use of a different separation unit other than a microfiltration apparatus would be expected to find utility and be encompassed by the appended claims. Different contaminated MEG streams other than those described herein may nevertheless be treated and handled in other non-restrictive embodiments of the invention adapted by one having ordinary skill in the art for those streams.

The present invention may suitably comprise, consist or consist essentially of the elements disclosed and may be practiced in the absence of an element not disclosed.

The words "comprising" and "comprises" as used throughout the claims is to interpreted "including but not limited to".

What is claimed is:

1. A monoethylene glycol (MEG) reclamation apparatus comprising not necessarily in this sequence:
   a seeding vessel having a vessel inlet, a solids drain line and a vessel outlet, where the vessel inlet is adapted to receive a mixture from a mixture conduit;
   a filtration unit having a feed inlet, a solids outlet, a recycle outlet and a permeate outlet;
   a seeded effluent conduit from the vessel outlet to the feed inlet on the filtration unit; and
   a recycle seeding conduit from the recycle outlet of the filtration unit to the mixture conduit.

2. The apparatus of claim 1 further comprising a seeded effluent recycle line from the seeded effluent conduit to the recycle seeding conduit.

3. The apparatus of claim 1 further comprising a mixer in the mixture conduit upstream from a point where the recycle seeding conduit joins the mixture conduit.

4. The apparatus of claim 3 further comprising a contaminated MEG feed line, a carbonate feed line and a base feed line joining at or prior to the mixer.

5. A monoethylene glycol (MEG) reclamation system comprising:
   a wet MEG surge drum having a contaminated MEG stream connected to
   the MEG reclamation apparatus of claim 1 at the vessel inlet, in turn having a permeate line from the permeate outlet connected to
   a MEG feed preheater having an effluent line connected to a MEG flash separator, in turn having a conduit connected to
   a MEG distillation column.

6. A method for reclaiming a monoethylene glycol (MEG), comprising not necessarily in this sequence:
   contacting an alkaline earth metal salt-contaminated MEG stream with an alkali metal carbonate and a base to form a mixture;
   contacting the mixture with recycled alkaline earth metal carbonate seeds to form a feed;
   routing the feed to a seeding vessel for growing alkaline earth metal carbonate particles;
   transmitting a seeded effluent from the seeding vessel to a filtration unit;
   discharging alkaline earth metal carbonate solids from the filtration unit;
   producing a reclaimed MEG stream from the filtration unit; and
   recycling alkaline earth metal carbonate seeds from the filtration unit to the feed.

7. The method of claim 6 further comprising preloading the seeding vessel with MEG containing alkaline earth metal carbonate particles.

8. The method of claim 6 further comprising mixing the alkali metal salt-contaminated MEG stream with the alkaline earth metal carbonate and the base to give the feed.

9. The method of claim 8 where the alkaline earth metal carbonate particles grow to an average particle size of at least 10 microns before the seeding effluent egresses the seeding vessel.

10. The method of claim 6 where:
    the alkaline earth metal salt comprises calcium chloride;
    the alkali metal carbonate comprises sodium carbonate;
    the base comprises sodium hydroxide; and
    the alkaline earth metal carbonate seeds comprise calcium carbonate seeds.

11. The method of claim 6 where the flow rate through the seeding vessel ranges from 40 gpm to 120 gpm (150 to 455 liters per minute).

12. A monoethylene glycol (MEG) reclamation apparatus comprising:
    a seeding vessel having a vessel inlet, a solids drain line and a vessel outlet where the vessel inlet is adapted to receive a mixture from a mixture conduit;
    a contaminated MEG feed line, a carbonate feed line and a base feed line joining to form the mixture conduit;
    a filtration unit having a feed inlet, a solids outlet, a recycle outlet and a permeate outlet;
    a seeded effluent conduit from the vessel outlet to the feed inlet on the filtration unit;
    a recycle seeding conduit from the recycle outlet of the filtration unit to the mixture conduit; and
   a seeded effluent recycle line from the seeded effluent conduit to the recycle seeding conduit.

13. The apparatus of claim 12 further comprising a mixer in the mixture conduit downstream from the contaminated MEG feed line, carbonate feed line and base feed line and upstream from a point where the recycle seeding conduit joins the mixture conduit.

14. A method for reclaiming monoethylene glycol (MEG), comprising not necessarily in this sequence:
    contacting an alkaline earth salt-contaminated MEG stream with an alkali metal carbonate and a base to form a mixture;
    contacting the mixture with recycled alkaline earth metal carbonate seeds to form a feed;
    preloading the seeding vessel with MEG containing alkaline earth metal carbonate particles;
    routing the feed to a seeding vessel for growing alkali metal carbonate particles, where the flow rate through the seeding vessel ranges from about 40 gpm to about 120 gpm (about 150 to about 455 liters per minute), transmitting a seeded effluent from the seeding vessel to a filtration unit after the alkali metal carbonate particles grow to an average particle size of at least about 10 microns;

discharging alkaline earth metal carbonate solids from the filtration unit;

producing a reclaimed MEG stream from the filtration unit; and recycling alkaline earth metal carbonate seeds from the filtration unit to the feed.

15. The method of claim 14 further comprising mixing the alkali metal salt-contaminated MEG stream with the alkaline earth metal carbonate and the base to give the feed.

16. The method of claim 14 where:
the alkaline earth metal salt comprises calcium chloride;
the alkali metal carbonate comprises sodium carbonate;
the base comprises sodium hydroxide; and
the alkaline earth metal carbonate seeds comprise calcium carbonate seeds.

* * * * *

UNITED STATES PATENT AND TRADEMARK OFFICE
CERTIFICATE OF CORRECTION

| | | |
|---|---|---|
| PATENT NO. | : 8,329,963 B2 | Page 1 of 1 |
| APPLICATION NO. | : 12/671263 | |
| DATED | : December 11, 2012 | |
| INVENTOR(S) | : James C. T. Chen | |

It is certified that error appears in the above-identified patent and that said Letters Patent is hereby corrected as shown below:

At column 2, line 33, please delete "alkali", and insert therefor -- alkaline earth --.

Signed and Sealed this
Twelfth Day of February, 2013

Teresa Stanek Rea
*Acting Director of the United States Patent and Trademark Office*